United States Patent [19]

Thiebaut

[11] Patent Number: 4,979,642
[45] Date of Patent: Dec. 25, 1990

[54] SPRAYER FOR STERILE PRODUCTS, MORE PARTICULARLY FOR ASEPTIC SOLUTIONS USED IN MEDICAL AND SURGICAL TREATMENTS

[75] Inventor: Jean-Marc Thiebaut, Loos, France

[73] Assignee: Centre Régional de Transfusion Sanguine de Lille, Lille Cedex, France

[21] Appl. No.: 209,569

[22] Filed: Jun. 21, 1988

[30] Foreign Application Priority Data

Jun. 22, 1987 [FR] France ................................ 87 08705

[51] Int. Cl.⁵ ............................................ B67D 5/06
[52] U.S. Cl. ..................................... 222/81; 222/382; 222/464; 215/247
[58] Field of Search ................... 222/80, 81, 211, 382, 222/383, 402.1, 464, 635; 141/2, 3, 18, 20; 215/247; 604/310, 416

[56] References Cited

U.S. PATENT DOCUMENTS

| 1,783,956 | 12/1930 | Cook | 604/416 |
|---|---|---|---|
| 2,564,400 | 8/1951 | Hall | 222/464 |
| 2,753,868 | 7/1956 | Seemar | 604/416 |
| 3,112,846 | 12/1963 | Hein | 222/402.16 |
| 3,141,583 | 7/1964 | Mapel et al. | 222/83.5 |
| 4,121,735 | 10/1978 | Wittersheim | 141/20 |
| 4,427,039 | 1/1984 | Brooks et al. | 141/20 |

FOREIGN PATENT DOCUMENTS

| 2437217 | 4/1980 | France . |
|---|---|---|
| 897240 | 3/1983 | France . |
| WO86/01731 | 3/1986 | World Int. Prop. O. . |

Primary Examiner—H. Grant Skaggs
Assistant Examiner—Steven Reiss
Attorney, Agent, or Firm—Burns, Doane, Swecker & Mathis

[57] ABSTRACT

The invention provides a spray for sterile products, more particularly aseptic solutions used in medical and surgical treatments. The spray, comprising a flask whose main orifice is closed by a precompression pump (2), and has another orifice (9) located in its lower part and closed sealingly by a stopper (10) made from a flexible and perforable material which remains sealing after perforation, said stopper and said flask having a special configuration promoting spraying of the last drops contained in the container.

21 Claims, 2 Drawing Sheets

SPRAYER FOR STERILE PRODUCTS, MORE PARTICULARLY FOR ASEPTIC SOLUTIONS USED IN MEDICAL AND SURGICAL TREATMENTS

BACKGROUND OF THE INVENTION

1. Field of the Invention

The invention relates to a spray for sterile products and more particularly for aseptic solutions used in medical and surgical treatments, such for example as sterile glues.

2. Description of Related Art

For treating the skin, and more especially the reconstitution of the skin of burned persons or more generally for surgical operations using epidermal or parenchymatous tissue, there exist solutions obtained for example from calcic thrombin mixed with a fibrinogen, which must be applied to the diseased zones under perfect aseptic conditions. For that, spraying devices are used giving a better distribution of the product and are less traumatic for the sick person A problem however arises because these products resulting from the mixture of two components must be prepared extemporaneously, a few moments before the treatment For that, the contents of a second flask containing the fibrinogen could be simply poured into a first flask containing the calcic thrombin solution, then the two components could be mixed and poured into a spraying flask, all these operations of course being carried out in a sterile atmosphere and with the greatest precautions. Since this kind of handling is difficult, a mixing unit could be used which avoids unstoppering flasks and transferring liquids from one to the other, and which would comprise for example a flask with two superimposed compartments, fitting one to the other and means for instilling the contents from one into the solution of the other, for example by means of a deformable member. Such a unit, however, does not exclude the transfer to a spraying container or the fitting of a spray to this unit ; there is then still a danger of spilling the product, or at least not handling it under perfectly sterile conditions. In addition, since the two mixed components induce a polymerization reaction, setting of the mixture is possible.

To overcome such drawbacks, there exists a spraying system formed of two syringes, each filled with one of the fluids to be mixed, mounted on the same support, the end adapters of which cooperate with a spraying head projecting the two products simultaneously. But the assembly formed by the syringes, the support and the special spraying head, is a specific product which is costly and difficult to use. Furthermore, this system requires a surrounding infrastructure, which makes it unusable outside appropriate medical rooms or operating theaters, since gas intakes, pressure reducers and all necessary control devices are required.

OBJECTS AND SUMMARY OF THE INVENTION

One of the aims of the invention was then to create a spray for sterile products, which is simple to use, which is also easy to handle and inexpensive to produce, the filling of which can be carried out in sterile conditions and which allows a product to be sprayed which is prepared extemporaneously, for any medical and surgical treatment and which thus avoids any infrastructure for its utilization. In the case of biological glue applications, this spray makes possible the sequential and independent spraying of the fibrinogen and calcic thrombin solutions inducing on the treated tissue the rapid appearance of a flow of resistant fibrin.

One object of the present invention consists then in providing a spray for sterile products comprising a flask for collecting the solution to be sprayed and on an orifice of which is fixed a distribution head for spraying the liquid by means of a propulsive agent or by the mechanical action of the piston of a precompression pump, said flask having another orifice located in its lower part and closed sealingly by a member made from a perforable flexible material which remains sealing after perforation, in which spray said perforable member is a stopper of special configuration closing the other orifice also of special shape so that the stopper and the perforable flexible material at the level of the orifice cooperate with each other to promote the recovery of the last drops contained in the container for spraying same.

Advantageously, the perforable flexible material is in the form of a tube with two necks and two identical opposite orifices closed by the same stopper made from a perforable flexible material which remains sealed after perforation.

According to particular features of the invention, the stopper has a lower part in the form of a disk corresponding to the diameter of the orifice and an upper part situated inside the flask and pierced with a central well. Furthermore, the stopper is provided with vertical lateral indentations extending over the whole of its height along the side, which indentations communicate through transverse channels with the central well.

BRIEF DESCRIPTION OF THE DRAWINGS

Other features and advantages of the invention will be clear from the following description of nonlimitative embodiments, with reference to the accompanying drawings which show :

In FIG. 1 an aerosol type sprayer is shown which comprises essentially a flask 1 whose upper orifice 8 is sealed by a precompression pump 2. The pump comprises essentially a cap 3 crimped to the flange of orifice 8, a plunger tube 4 which extends as far as the lower part of the flask and which communicates at the top with a distribution head 3 and a small stop valve 6. The head 5, which generally includes appropriate spraying nozzles, controls the opening of the small valve 6 against the force of a spring 7, which allows the liquid to pass from tube 4 to the head under the action of a pressure exerted on the head of the pump.

Figure 1:
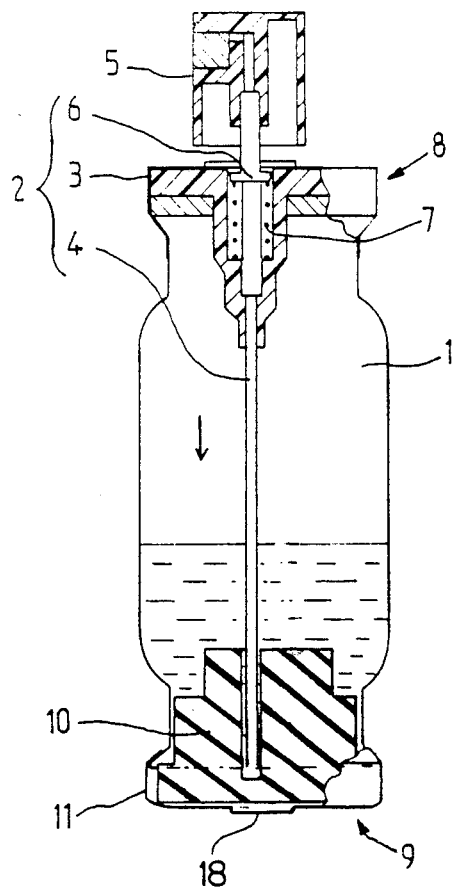
FIG. 1 is a schematical sectional view of a sprayer.
Figure 2:
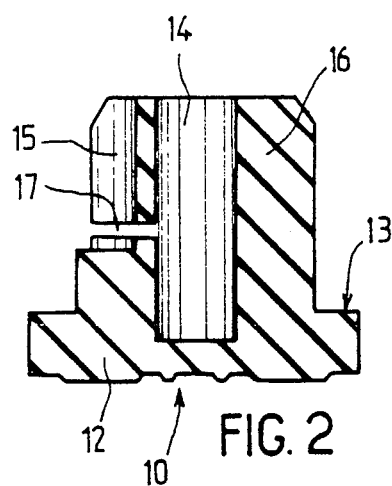
FIG. 2 is a sectional view on a larger scale through II—II of FIG. 3.
Figure 3:
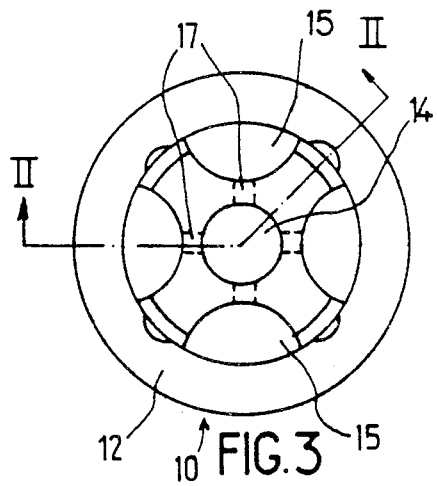
FIG. 3 is a top view of the lower stopper.
Figure 4:
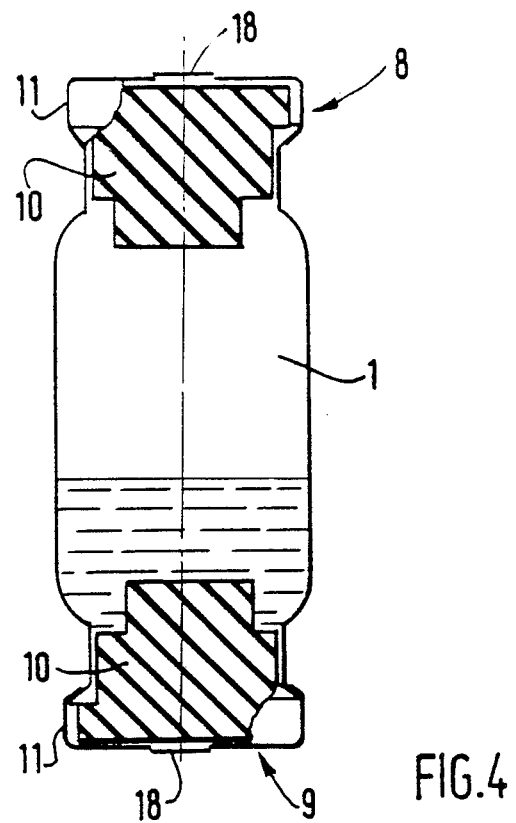
FIG. 4 is a variant of a spraying flask.

The flask 1 has at its lower part another orifice 9 closed by a stopper 10. This stopper, of special structure, is shown in detail in FIGS. 2 and 3. It sealingly closes orifice 9 and is held in position by an annular cap 11 crimped to the flange of this orifice, which cap does not cover the whole surface of the stopper and leaves the central part thereof visible. A tamperproof capsule 18 is crimped on this annular cap. The stopper is made from a perforable flexible material having the property of providing good sealing along a perforating member, and resuming its initial form after perforation while remaining sealed. The lower part 12 of stopper 10, in the form of a disk, corresponding to the diameter of orifice 9, is held in position by a shoulder 13 between the cap 11 and the flange of orifice 9. The upper part 16 of the stopper, which is situated inside the flask, is provided with a central well 14 whose bottom is substantially at the level of disk 12. Four indentations 15 with rounded profile extend over the whole height and along the sides of a stopper, at 90° from each other, parallel to well 14. Each has passing therethrough, substantially at mid-height, channels 17 which communicate the indentations with well 14. It will be noted that the lower part of flask 1 in the zone peripheral to stopper 10, i.e., the bottom part of the flask, has a profile in the shape of a funnel for recovering the last drops of the liquid at the bottom of the flask at the level of the central well 14. The lower end of tube 4 extends into the central well and opens into this lower central zone of the stopper.

Before spraying a mixture with this spray, the mixture it is prepared extemporaneously and is introduced into the flask from which the capsule 18 has been previously removed by stabbing through the stopper 10. After the syringe has been withdrawn, stopper 10 closes again and remains sealing. The mixture may be sprayed by operating the distribution head 5. Considering the structure of stopper 10, the last drops of the product, gathered together at the bottom of well 14, may be recovered by tube 4 and sprayed.

In the case where a source of nitrogen is available on the spot, when the treatment is to be carried out for example in a hospital, the flask may obviously be provided with a propulsive gas. For that, the lower stopper 10 of the spray would have a duct passing sealingly therethrough for supplying a propulsive gas, for example nitrogen, coming from a generator.

In a variant illustrated in FIG. 4, the flask is in the form of a tube with two necks and two opposite orifices 8 and 9, advantageously of the same dimensions so that the upper orifice 8 of flask 1 may be closed by a stopper 10 identical to the stopper closing the lower orifice 9 and described above with reference to FIGS. 2 and 3, this upper stopper being also profiled for recovery of the liquid and being equipped with the same crimping cap 11, and closure capsule 18.

Said flask may be empty or filled with a liquid or lyophilized and sterile product When it is desired to spray a liquid from such a flask which is not prefilled with liquid, capsule 18 is removed from one of the two plugs, which is the upper stopper, then it is pierced with a needle which, like tube 4 of the first example, forms part of a spraying device not shown which clips on to the neck of the flask and covers the upper stopper and orifice 8. The end of said needle then comes into the central well of the lower stopper, like the plunger tube 4.

Then, after the capsule 18 has been removed from the lower stopper 10, the liquid which it is desired to spray is introduced by means of a syringe stabbing through the stopper. After removal of the syringe, the stopper closes again and remains sealing. The apparatus is then ready for spraying since the device has been fixed to the upper stopper. Since the whole of the spraying system has been sterilized, the danger of handling under conditions which are not perfectly sterile is eliminated.

Although only preferred embodiments are specifically illustrated and described herein, it will be appreciated that many modifications and variations of the present invention are possible in light of the above teachings and within the purview of the appended claims without departing from the spirit and intended scope of the invention.

I claim:

1. A sprayer for sterile products, comprising:
a flask for collecting a solution to be sprayed having a main orifice;
means mounted to the main orifice for spraying the solution;
said flask having a second orifice located in its lower part;
a stopper made from a perforable flexible material which remains sealed after perforation for closing the second orifice;
means for conveying the solution from the stopper of the second orifice to the spraying means;
said stopper and flask including means for enabling the stopper, the flask, and the conveying means to cooperate with each other at the level of the second orifice to promote the recovery of the last drops contained in the flask for spraying the same; and
the lower part of the flask adjacent the second orifice has a profile in the form of a funnel for bridging together the last drops of liquid at the level of the stopper for the second orifice.

2. The sprayer for sterile products according to claim 1, wherein the flask is in the form of a tube with two necks and two opposite orifices, further comprising a stopper for the main orifice, each of said stoppers being made from a perforable flexible material which remains sealed after perforation.

3. The sprayer according to claim 2, wherein the stopper for the second orifice is provided with vertical lateral indentations with rounded profile extending over the whole height and along the sides of the stopper.

4. The spray according to claim 2, wherein said spraying means is clipped onto the stopper of the main orifice, said spraying means having a needle for piercing the stopper.

5. The sprayer for sterile products according to claim 2, wherein the stopper has a lower part in the form of a disk corresponding to the diameter of the second orifice and an upper part which is situated inside the flask, said upper part being provided with a central well.

6. The sprayer for sterile products according to claim 2, wherein the two orifices and stoppers are of the same dimensions.

7. The sprayer according to claim 6, wherein the stopper for the second orifice is provided with vertical lateral indentations with rounded profile extending over the whole height and along the sides of the stopper.

8. The sprayer for sterile products according to claim 1, wherein the stopper for the second orifice has a lower part in the form of a disk corresponding to the diameter of the second orifice and an upper part which is situated inside the flask, said upper part being provided with a central well.

9. The sprayer according to claim 8, wherein the stopper for the second orifice is provided with vertical lateral indentations with rounded profile extending over the whole height and along the sides of the stopper.

10. The sprayer according to claim 9, wherein each indentation has passing therethrough, substantially at mid-height, channels which place them in communication with the central well.

11. The sprayer according to claim 1, wherein the stopper is provided with vertical lateral indentations with rounded profile extending over the whole height and along the sides of the stopper.

12. The sprayer according to claim 1, wherein said spraying means is clipped on to a stopper of the main orifice, said spraying means having a needle for piercing the stopper of the main orifice.

13. A sprayer for liquids, comprising:
a flask having a first orifice at one end and a second orifice at a second end thereof;
means mounted in said first orifice for spraying liquid from said flask, said spraying means including a stem having an end extending substantially to the second end of the flask; and
means in said second orifice for sealing closed the second orifice, said sealing means being made of a perforable flexible material that is capable of being perforated by a syringe for purposes of filling the flask and which is further capable of resealing itself after the syringe is withdrawn;
said sealing means having means for collecting the last few drops of liquid in the flask at a location adjacent the end of the stem; and
the lower part of the flask adjacent the second orifice has a profile in the form of a funnel for bringing together the last drops of liquid at the sealing means for the second orifice.

14. The sprayer according to claim 13, wherein the collecting means includes a well formed in said sealing means for collecting the liquid.

15. The sprayer according to claim 14, further including channels extending through walls of said collecting means for facilitating the collection of liquid in said well.

16. A flask for sterile products, comprising
a central portion and first and second orifices at opposite sides of said central portion, said first and second orifices being substantially similar in size and shape;
a first stopper arranged in said first orifice for closing said orifice, said first stopper comprising a perforable flexible material which remains sealed after perforation; and
a second stopper arranged in said second orifice for closing said second orifice, said second stopper being substantially similar to said first stopper;
each of said first and second stoppers includes:
an upper part situated inside the flask that is provided with a central well;
lateral indentations located radially outwardly of said well and parallel to said well; and
each indentation has passing therethrough, substantially at mid-height, a channel which places it in communication with the central well.

17. The flask of claim 16, wherein each of the stoppers has a lower part in the form of a disk corresponding to the diameter of the respective orifice, and an upper part which is situated inside the flask, said well being located in the upper part of the stopper.

18. A sprayer for sterile products, comprising:
a flask for collecting a solution to be sprayed having a main orifice;
means mounted to the main orifice for spraying the solution;
said flask having a second orifice located in its lower part;
a stopper made from a perforable flexible material which remains sealing after perforation for closing the second orifice;
means for conveying the solution from the stopper of the second orifice to the spraying means, said conveying means having a collecting end adjacent the second orifice;
said stopper and flask including means for enabling the stopper, the flask, and the conveying means cooperate with each other at the level of the second orifice to promote the recovery of the last drops contained in the flask for spraying same;
said enabling means including vertical laterally indented flow means along the sides of the stopper for facilitating collecting the last few drops of liquid at the collecting end of the conveying means.

19. The sprayer for sterile products according to claim 18, wherein the flask is in the form of a tube with two necks and two opposite orifices, further comprising a stopper for the main orifice, each of said stoppers being made from a perforable flexible material which remains sealed after perforation.

20. The sprayer for sterile products according to claim 19, wherein the two orifices and stoppers are of the same dimensions.

21. The sprayer for sterile products according to claim 18, wherein the stopper for the second orifice has a lower part in the form of a disk corresponding to the diameter of the second orifice and an upper part which is situated inside the flask, said upper part being provided with a central well.

* * * * *